United States Patent [19]
Fortin et al.

[11] Patent Number: 5,674,070
[45] Date of Patent: Oct. 7, 1997

[54] TEETH PROSTHESIS, METHOD OF MANUFACTURE THEREOF, METHOD FOR MOUNTING AND REMOVING A SUPRASTRUCTURE THEREOF AND KIT USEFUL FOR THE MANUFACTURE OF THE TEETH PROSTHESIS

[75] Inventors: Yvan Fortin, 3989 Lac Sept-Iles Sud, St-Raymond de Portneuf, Canada, G0A 4G0; Bjarne Kvarnstrom, Hinsdale, Ill.

[73] Assignee: Yvan Fortin, Saint-Raymond-de-Portneuf, Canada

[21] Appl. No.: 429,760

[22] Filed: Apr. 27, 1995

Related U.S. Application Data

[63] Continuation-in-part of Ser. No. 193,426, Feb. 8, 1994, Pat. No. 5,429,505.

[51] Int. Cl.[6] .................................................. A61C 13/12
[52] U.S. Cl. .................................................. 433/172; 433/173
[58] Field of Search .................................. 433/172, 173, 433/193, 195

[56] References Cited

U.S. PATENT DOCUMENTS

| | | | |
|---|---|---|---|
| 2,644,231 | 7/1953 | Brennan | 433/173 |
| 3,748,739 | 7/1973 | Thibert | 433/173 |
| 4,085,506 | 4/1978 | Lew | 433/173 |
| 4,763,791 | 8/1988 | Halverson et al. | 206/570 |
| 4,904,186 | 2/1990 | Mays | 433/172 |
| 4,931,016 | 6/1990 | Sillard | 433/172 |
| 5,234,341 | 8/1993 | Johansen | 433/173 |

FOREIGN PATENT DOCUMENTS 1340429 9/1963 France .

OTHER PUBLICATIONS

Advertising document entitled "Spark Erosion System" from Dental Arts Laboratories, Inc. (No date).
"Prothese Dentaire", No. 52, Feb. 1991, pp. 27–38 MK1 Fastener, Polybental Laboratory, Brussels, Belgium.
"Removable Closure of the Interdental Space (C.I.S.)", Arnold A. Gaerny, Translated from the revised and enlarged German edition by Thomas M. Hassell, D.D.S., Zurich, Switzerland, Published in Berlin and Chicago, 1972.

Primary Examiner—Cary E. O'Connor
Attorney, Agent, or Firm—Merchant, Gould, Smith, Edell, Welter & Schmidt, P.A.

[57] ABSTRACT

A teeth prosthesis for an upper maxilla includes an infrastructure, a suprastructure, and an assembly for a removable attachment of the suprastructure with the infrastructure. The infrastructure includes at least three implants, one connection bar, and an assembly for removably fastening the connection bar with and against each head of the implants. The suprastructure includes a first member made of cast metal or alloy having an intrados provided with an opening giving access to a housing of such size and depth to allow the housing of the connection bar therein, a second member immovably attached with the first member, and a set of teeth immovably attached with the first member and the second member. The assembly includes two first fastening members, and a second fastening member. The invention is also directed to a method for the manufacture of such a teeth prosthesis and to a kit comprising prefabricated parts useful for the manufacture of the prosthesis.

29 Claims, 11 Drawing Sheets

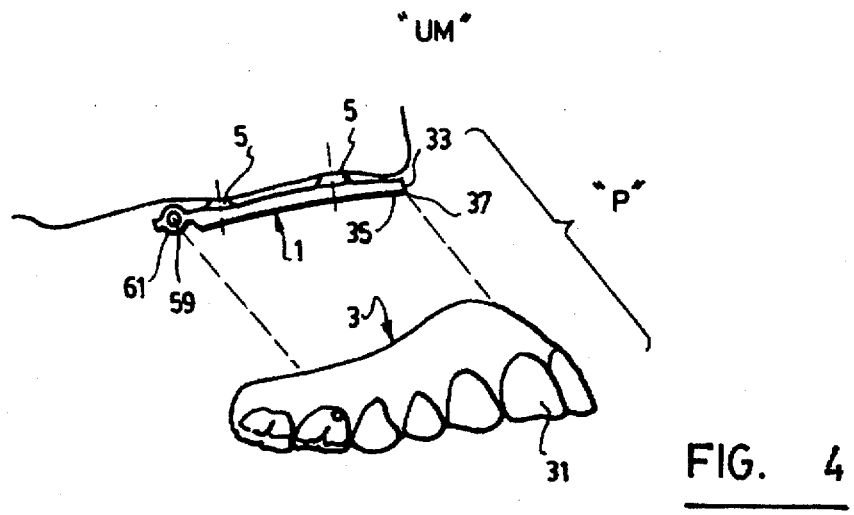
FIG. 4
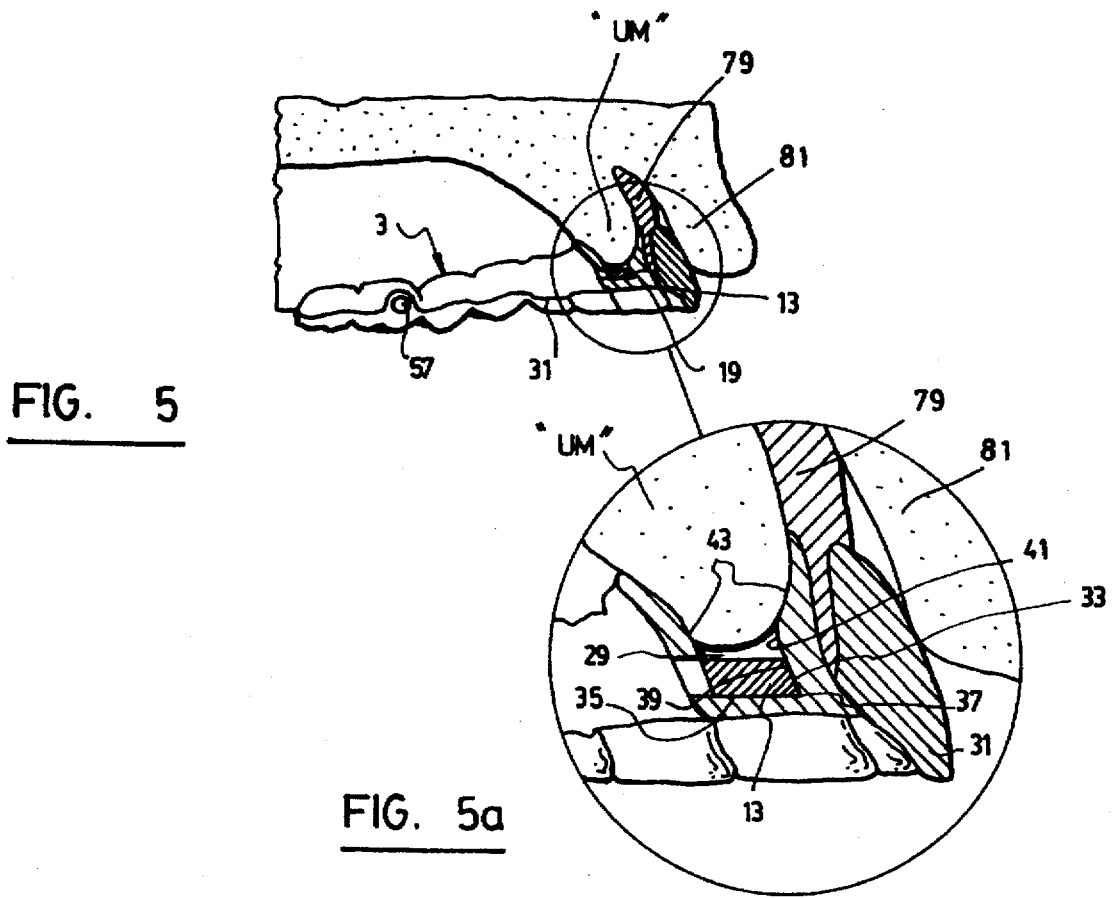
FIG. 5
FIG. 5a

TEETH PROSTHESIS, METHOD OF MANUFACTURE THEREOF, METHOD FOR MOUNTING AND REMOVING A SUPRASTRUCTURE THEREOF AND KIT USEFUL FOR THE MANUFACTURE OF THE TEETH PROSTHESIS

This is a Continuation-In-Part of U.S. application Ser. No. 08/193,426, filed 8 Feb. 1994, now U.S. Pat. No. 5,429,505, which application is incorporated herein by reference.

BACKGROUND OF THE INVENTION

1. Field of the Invention

The present invention relates to an improved teeth prosthesis for an upper maxilla, to a method of manufacture thereof, and to a method for mounting or removing a suprastructure of said prosthesis on or from a fixed infrastructure. Also, the invention relates to a kit comprising prefabricated parts useful for the manufacture of an improved teeth prosthesis for an upper maxilla according to the invention.

2. Brief Description of the Prior Art

It is known in the art to embody teeth prosthesis for a lower maxilla, said teeth prosthesis being of the type comprising an infrastructure, a suprastructure and means for a removable attachment of the suprastructure with the infrastructure.

The infrastructure comprises:
- at least two implants, advantageously at least 3 and preferably four to six, each implant having opposite ends, one end of each implant being anchored in the bone of the lower maxilla while the opposite end is sticking out of the gingiva and defines a head to said implant,
- one connection bar having a fore part and two opposite rear ends, said connection bar being shaped and sized to be substantially facing the gingiva of the lower maxilla, and
- means for removably fastening the connection bar with and against each head of maid implants.

The suprastructure comprises:
- a member made of metal or alloy, such as cast metal or alloy, maid member having a fore part and two rear ends, maid member having an intrados provided with an opening giving access to a housing provided in the member, said housing being of much size and depth to allow the connection bar to be housed therein,
- a saddle immovably attached with the member, and
- a set of teeth immovably attached with the member and the saddle.

The means for a removable attachment of the suprastructure with the infrastructure comprises fastening means that are respectively immovably attached with a corresponding rear end of the member, for removably attaching them with corresponding ends of the connection bar. Preferably such fastening means comprises:
- a device comprising a sleeve, especially a cylindrical sleeve, immovably attached with a corresponding end of the member, said cylindrical sleeve being provided with a lateral opening, and a pin slidably mounted inside the sleeve and movable between two distinct positions, a first distinct position being defined when the pin is not facing the lateral opening and a second distinct position being defined when the pin is facing the lateral opening,
- a bore provided in a protuberance, especially a small protuberance, near a corresponding end of the connection bar, said protuberance being shaped and sized to be housed in a corresponding cylindrical sleeve through the lateral opening of said cylindrical sleeve, to be co-axial with a longitudinal axis of the cylindrical sleeve and to be removably engaged by the pin.

Advantageously, each of aforesaid fastening means are of the type of those sold under the trade mark MK1 (Polydental Laboratory, BELGIUM).

However, even though aforesaid prior art teeth prosthesis can work correctly when installed on the lower maxilla, it become unusable for the upper maxilla because it was not possible to prevent the fore part (i.e. the anterior part) of the suprastructure to separate from the infrastructure without having to negatively affect the aesthetic appearance of the fore part of said prosthesis. In fact there is generally not enough space to provide a conventional lock at the anterior part.

Therefore, there was a very strong need for a way allowing to efficiently fasten the fore part of a suprastructure of a teeth prosthesis for an upper maxilla, comprising a fixed infrastructure and a removable suprastructure, without affecting the aesthetic characteristic of the fore part of said suprastructure.

Also, there was a strong need to obtain a simple and easy method for mounting and removing a suprastructure of a teeth prosthesis for an upper maxilla. Indeed, methods actually known for mounting and removing a suprastructure on or from an fixed infrastructure are laborious.

SUMMARY OF THE INVENTION

A first object of the present invention is to provide a teeth prosthesis that can be easily, efficiently and safely installed on the upper maxilla, said prosthesis having a fixed infrastructure and a removable suprastructure that can be easily mounted on the infrastructure or removed from said infrastructure.

Another object of the present invention is to provide a teeth prosthesis where the fore part of the suprastructure can not separate from the fore part of the infrastructure when the rear portions of the suprastructure are attached with corresponding portions of a connection bar which is part of the infrastructure.

Another object of the present invention is to provide a teeth prosthesis where the person wearing it can has the feeling of having its own original teeth of the upper maxilla.

Another object of the present invention is to provide a teeth prosthesis which is further provided on its suprastructure, with means allowing to support the upper lip and then prevent any disformation of the same.

Another object of the present invention is to provide a teeth prosthesis where the person wearing it can easily remove the suprastructure for cleaning and hygiene purposes and then easily remount said suprastructure.

Another object of the present invention is to provide a method for easily mounting or removing the suprastructure of a teeth prosthesis defined hereinbefore as being part of the invention.

Another object of the present invention is to provide a teeth prosthesis for an upper maxilla that works exactly as a fixe bridge and has at once the some advantages of a fixed bridge and all the advantages of a removable bridge.

Another object of the invention object is to provide a teeth prosthesis for a upper maxilla having a suprastructure which closely cooperates with the infrastructure so as to minimize or prevent the wear that may result from the contact between two parts of the prosthesis and thus increase the life time of said prosthesis.

Another object of the invention is a teeth prosthesis for an upper maxilla having an infrastructure which may be suitable to a large variety of upper gingiva configuration.

Another object of the invention is a teeth prosthesis for an upper maxilla which is hygienic, aesthetic, and allow the person wearing it to have a good pronunciation.

Another object of the invention is to provide a kit comprising prefabricated parts useful for the manufacture of a teeth prosthesis according to the invention.

Another object of the invention is to provide a method for manufacturing a teeth prosthesis according to the invention.

More particularly, the invention relates to a teeth prosthesis for an upper maxilla, said prosthesis comprising a fixed infrastructure, a suprastructure and means for a removable attachment of the suprastructure with the infrastructure;

said infrastructure comprising:

at least three implants, preferably at least four, each implant having opposite ends, one end of each implant being anchored in the bone of the upper maxilla while the opposite end is sticking out of the gingiva and defines a head to said implant, one connection bar having a fore part and two opposite rear ends, said bar being shaped and sized to be substantially facing the gingiva of the upper maxilla, means for removably fastening the connection bar with and against each held of said implants;

said suprastructure comprising:

a first member made of metal or alloy, having a fore part and two rear ends and having an intrados provided with an opening giving access to a housing of such size and depth to allow the connection bar to be housed therein;

a second member immovably attached with the first member, said first and second members defining together a saddle;

a set of teeth immovably attached with the first member and the second member;

said means for a removable attachment of the suprastructure with the infrastructure comprising:

two first fastening means that are respectively attached with a corresponding rear end of the first member for removably attaching them with corresponding ends of the connection bar, a second fastening means comprising a first sliding face provided on the fore part of the connection bar and inclined toward the rear of said connection bar, a lower part of said face forming with a bottom face of said connection bar an edge projecting ahead the connection bar, and a second sliding face provided on a fore wall of the housing of the first member, said sliding faces, when the first and second fastening means are attached with the connection bar, cooperating together to lock the fore wall of the first member against the fore part of the connection bar and press a fore part of the saddle against the corresponding portion of gingiva of the upper maxilla.

Optionally, one or several of said implants may be two part implants of the type comprising a lower part anchored in the bone and an upper part sticking out the gingiva. Both parts are removably fastened together.

The invention also relates to a kit comprising prefabricated parts useful for the manufacture of a teeth prosthesis as defined hereinabove. The kit comprises at least one two part insert. This two part insert comprises a female part and a male part which are manufactured to fit closely one into the other. The male part and the female part may be removably secured together with securing means. This two part insert corresponds to the second fastening means of the teeth prosthesis of the invention and the male part is to be an integral part of the connection bar and the female part is to be an integral part of the first member.

The invention further relates to a method for the manufacture of a teeth prosthesis according to the invention and defined hereinabove. According to that method, the connection bar of the infrastructure and the suprastructure are obtained according to the following steps:

a) building a pattern of a connection bar with reference to a matrix which is a duplicate of the gingiva of an upper maxilla provided with at least three implants, then removing at least one portion of said pattern, said portion substantially corresponding to a male part of a two parts insert, said two part insert comprising a female part and the male part and both parts being manufactured to fit closely one into the other, the male part and the female part being further removably securable together with securing means and corresponding to said second fastening means;

b) obtaining one moulded member or several moulded member parts by casting of a metal or alloy in one or several moulds corresponding to the pattern or corresponding to parts of the pattern, and then fastening it or them to the male part to thus define said connection bar;

c) building a first member mould from a matrix which is a duplicate of the gingiva of the upper maxilla provided with at least three implants, the connection bar and the female part of the two part insert secured thereon;

d) obtaining the first member by casting a metal or alloy thereof in the mould to fill this latter and then removing the resulting first member;

e) removing the female part from the male part incorporated in the connection bar, and then fastening it with the first member so as to be engageable by said male part incorporated in the connection bar; and f) positioning and securing the teeth, the saddle and the first fastening means on the first member to thus define the suprastructure.

The invention also relates to a method of use of a teeth prosthesis as defined hereinbefore, wherein:

for mounting the suprastructure on the infrastructure, one only have to move both sliding surface one against the other and to fasten the rear ends of the first member with the corresponding rear ends of the connection bar;

for removing the suprastructure from the infrastructure, one only have to unfasten the rear ends of the first member from the corresponding rear ends of the connection bar and to move the sliding faces away from each other.

BRIEF DESCRIPTION OF THE DRAWINGS

The invention will be better understood with reference to the following non-restrictive description of preferred embodiments thereof, taken in connection with the accompanying drawings.

FIG. 4 is an exploded side elevational view of the suprastructure and the infrastructure of a teeth prosthesis according to the invention with a partial illustration of the upper maxilla;

FIG. 5 is a longitudinal cross-sectional view of a teeth prosthesis according to the invention with a partial illustration of the upper maxilla and of the upper lip;

FIG. 5a is an enlarge view of a part of FIG. 5;

DESCRIPTION OF PREFERRED EMBODIMENTS

Figure 1:
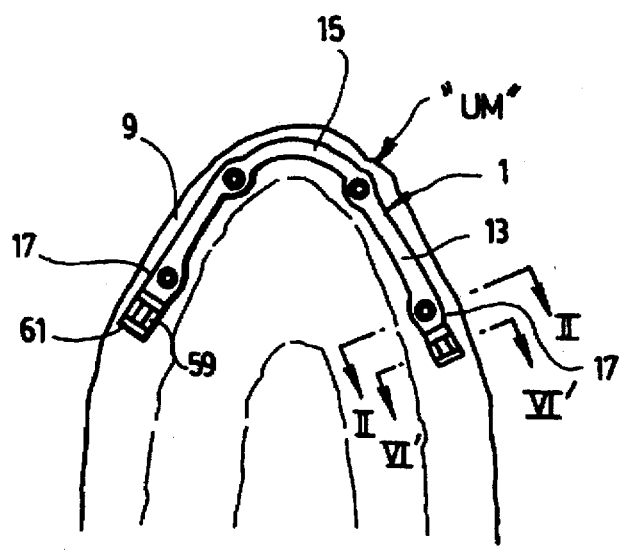
FIG. 1 is a bottom plan view of the infrastructure of a teeth prosthesis according to the invention with a partial view of the upper maxilla.
Figure 2:
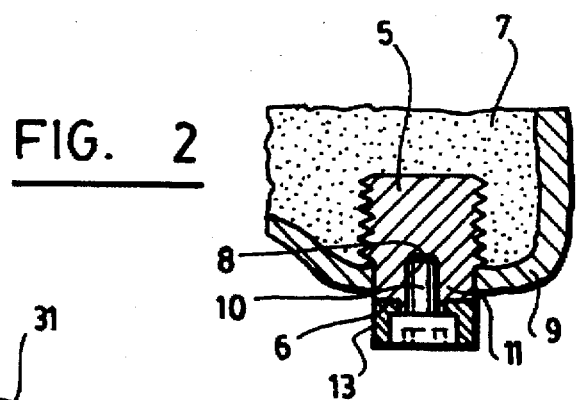
FIG. 2 is a cross sectional view according to line II—II in FIG. 1.

In order to make easier the reading of the following description of the preferred embodiments of the invention and because the embodiment represented on FIGS. 1 to 8, on one hand, and on FIGS. 8 to 21 on the other hand, present a plurality of similar structural parts, identical but incremented reference numbers were used. Thus, for example, the connection bar 13 appearing on FIG. 1 is numbered 113 on FIG. 8, and two opposite rear ends 17 appearing on FIG. 1 is numbered 117 on FIG. 8.

Referring to FIGS. 1 to 7, the invention relates to a teeth prosthesis "P" for an upper maxilla "UM", said prosthesis "P" comprising an infrastructure 1, a suprastructure 3 and means for a removable attachment of the suprastructure 3 with the infrastructure 1.

The infrastructure 1 comprises:

at least three implants 5, preferably four as illustrated, and more preferably 5 or 6 implants, each implant 5 having opposite ends, one end of each implant being anchored in the bone 7 of the upper maxilla while the opposite end is sticking out of the gingiva 9 defines a head 11 to said implant 5;

one connection bar 13 having a fore part 15 and two opposite rear ends 17, said connection bar 13 being shaped and sized to be substantially facing the gingiva 9 of the upper maxilla "UM"; and means for removably fastening the connection bar 13 with and against each head 11 of said implants 5.

Each implant 5 may be of the type of those well known and 10 recognized in the art and anchored in the bone of the upper maxilla according to technics well known to man skilled in the art. Said implant may be made of titanium metal or alloys.

The connection bar 13 is built in laboratory by waxing technique (i.e. thus custom made), except the fore part of said connection bar which is milled to define the inclined sliding face 33 and the edge 37. The milling of the connection bar 13 is achieved with a milling machine commonly used by dental laboratory and using usual drills and/or cutters. The technic for modeling the shape of a connection bar 13 with a milling machine is well known in the art and does not need to be explained in detail.

Preferably, each implant 5 may be further provided, as means for fastening the connection bar 13 with and against each head 11, with a shoulder 6 and a central threaded bore 8, the connection bar 13 being provided, of said implants, with an opening corresponding to a head 11, and for each implants a threaded screw 10 engaging the threaded bore 8 to press the connection bar 13 against the shoulder 6 and locked said connection baron said head 11. Advantageously, as illustrated, the connection bar 13 is at a small distance from the gingiva 9. Optionally, a spacing member (not shown) may be positioned between the head 11 and the connection bar 13, especially to adjust by distance between the gingiva 9 and said bar 13.

The suprastructure 3 comprises:

a first member 19 made of cast metal or alloy, and having a fore part 21 and two rear ends 23, having an intrados 27 provided with an opening giving access to a housing 29 provided in the member 19, said housing 29 being of such size and depth to allow the housing of the connection bar 13 to be housed therein, a second member 25 immovably attached with the first member 19, said members 19 and 25 defining together a saddle, and a set of teeth 31 immovably attached with the first member 19 and the member 25.

The means for a removable attachment of the suprastructure 3 with the infrastructure 1 comprises:

two first fastening means that are respectively immovably attached with a corresponding rear end 23 of the first member for removably attaching them with corresponding ends 17 of the connection bar 13, a second fastening means comprising a first sliding face 33 provided on the fore part 15 of the connection bar 13 and inclined toward the rear of said connection bar 13, a lower part of said face forming with a bottom face 35 of said connection bar 13 an edge 37 projecting ahead the connection bar 13, and a second sliding face 39 provided on a fore wall 41 of the housing 29 of the first member 19, said sliding faces 33 and 39, when the first and second fastening means are attached with the connection bar 13, cooperating together to lock the fore part 41 of the first member 19 against the fore part 15 of the connection bar 13 and press a fore part 43 of the suprastructure against the corresponding portion of gingiva 9 of the upper maxilla "UM"

More particularly each first fastening means respectively comprises:

- a device 51 that is immovably attached with a corresponding end of the member 19, said device 51 comprising a cylindrical sleeve 53 provided with a lateral opening 55, and a pin 57 slidably mounted inside the sleeve 53 and movable between two distinct positions, a first distinct position being defined when the pin 57 is not facing the lateral opening 53 and a second distinct position being defined when the pin 57 is facing the lateral opening 53,
- a bore 59 provided in a small protuberance 61 near corresponding end 17 of the connection bar 13, said protuberance 61 being shaped and sized to be housed in a corresponding cylindrical sleeve 53 through the lateral opening 55 of said cylindrical sleeve 53 and co-axial with a longitudinal axis of the cylindrical sleeve 53. The bore 59 is sized to be removably engaged by the pin 57.

Preferably, each cylindrical sleeve 53 and the pin 57 are both of such size to be completely housed between an inner and an outer lateral walls 71, 73 of the suprastructure 3, when the pin 57 is slid completely inside the cylindrical sleeve 53, and wherein a portion of the pin 57 projects from the corresponding inner wall 71 of the suprastructure 3 when the pin 57 is slid to be not facing the lateral opening 55 of the cylindrical sleeve 53, a first bore 75 co-axial with the longitudinal axis of the pin 57 being provided in the corresponding inner wall 71 of the suprastructure 3 to allow the passage of the pin 57 therethrough and a second bore 77 of size smaller than a diameter of the pin 57 and co-axial with the longitudinal axis of said pin S7 being provided in the corresponding outer wall 73 of the suprastructure 3, said second bore 77 allowing a small tool "T" to push the pin 57 from a distinct position where it faces the lateral opening 55 of the cylindrical sleeve 53 toward the other distinct position where said pin 57 does not face said lateral opening 55.

Advantageously, the metal or alloy used to from the first member 19 may be one of those well known in dentistry, especially gold or gold alloys or palladium or palladium alloys.

Advantageously, the material use to form the second member 25 may be one of plastic material especially resins, known to be use in dentistry. This second member 22 may be fastened on the first member by any appropriate technique well known and recognized is the art (e.g. gluing).

Advantageously, teeth are made with a usual material in the field of dentistry.

The housing 29 is obtained according to usual technics involving the use of a "matrix" identical to the shape of the infrastructure with the gingiva 9 and on which the infrastructure 1 is mounted and the first member 19 is cast within an appropriate mould. That technic is well known in the art and does not need to be explained in detail. Nevertheless, it must be noted that the "matrix" includes the "sliding surface" 33 and thereby forms, during the moulding, the sliding surface 39 in the housing 29 of the first member 19 to be obtained. Of course said housing 29 is formed by the presence of the connection bar 13 in the matrix. Furthermore, devices 51 may be mounted on the connection rod 13 so as to be surrounded by the moulded metal or alloy and then locked in the hardened first member 19. The outer surface of the sleeve 53 may be provided at this end with protuberances.

Advantageously, the suprastructure 3 may be further provided with a lip support 79. It may be made of plastic material especially resins known to be used in dentistry.

This lip support 79 allows to support the lip 81 of a person (see FIG. 5). The lip support 79 may be fastened on the first member by any appropriate techniques well known and recognized in the art (e.g. gluing). Preferably, the second member 25 and the lip support 79 are made in of single piece of material.

More particularly, with the prosthesis "P" defined hereinabove the following steps may be carried out:

for mounting the suprastructure 3 on the infrastructure 1, one only have to grasp the fore part 21 of the suprastructure 3 and put sliding faces 33, 39 one against the other, to house each protuberance 61 of the connection bar 13 in a corresponding housing of the member 19 to thus co-axially align the longitudinal axis of each bore 59 of the connection bar 13 with the longitudinal axis of a corresponding sleeve 53, and then to push each pin 57 with his finger or his tongue to slid them in their respective cylindrical sleeve 59 and through a corresponding bore 61 of the connection bar 13;

for removing the suprastructure 3 from the infrastructure 1. one only have to introduce a fine Pin 83 through the said bore 75 of the suprastructure 3 and push the pin 57 until it no longer face the lateral opening 53 of its corresponding cylindrical sleeve 53, to remove said fine pin 83 from said bore 75 and introduce it through the other bore 75 of the suprastructure 3 and push the pin 57 until it no longer face the lateral opening 5 of its corresponding cylindrical sleeve 53, and then to grasp the fore part 21 of the suprastructure 3 and remove both sliding faces 33, 39 from each other.

Preferably, when sliding faces are slid one against the other during the mounting of the suprastructure 3 on the infrastructure 1 or the removing of the suprastructure 3 from the infrastructure 1, said faces are moved substantially parallel. (i.e. thus the suprastructure 3 is moved with respect to the infrastructure 1 according to an angle substantially parallel with a plane containing said sliding surface 33).

When pieces are obtained by mouling techniques, it is difficult to obtain an accurate adjustment between the connection bar and the first member. This difficulty involve that some wear may occur between the connection bar and the first member. However, it was further found that this inconvenience may be overcome when at least the fore part of the connection bar is a machine portion incorporated in said connection bar and at least one corresponding machine is secured to the first member inside the housing. This association of the machine portion (defining a male part) of the connection bar with its corresponding machine member (defining a female part) of the first member defines said second fastening means. The male part fit closely into the female part to provide in connection with the first fastening means a three point supporting attachment of the suprastructure to the infrastructure that confer a great stability to the prosthesis and thus contribute to reduce the wear between the connection bar and the first member.

Preferably, additional association of machine portions and machine members may be provided so as to let the first fastening means to its sole role of fastening, the support being then provided by said additional associations. Preferably, there is two additional association. They differs from the one provided in the fore part of the prosthesis in that they are only design for supporting and positioning and not for fastening.

According to a particularly preferred embodiment of the invention and referring to FIG. 8 to 11, the prostesis "P'" has a connection bar 113 that may result from the fastening of male part 114 and male parts 192 with cast portions 112. Advantageously, protuberances 161 may be a machine portion belonging to a machine first fastening means 153. Said parts 114 and 192, and eventually machine protuberances 161, are fastened to the cast portions 112 by any appropriate means well known to man skilled in the art, especially welding.

Figure 8:
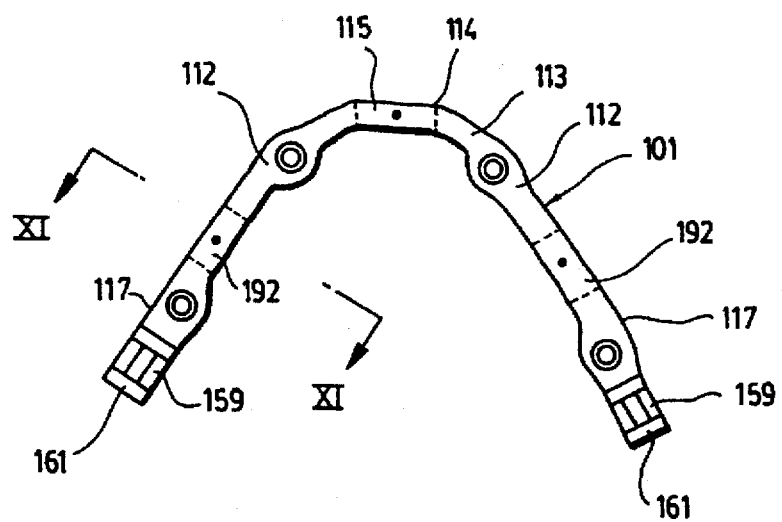
FIG. 8 is a top view of the of a connection bar with manufactured inserts included thereon according to a preferred embodiment of the invention.

The first of aforesaid association comprise a male part 114 and a female part 122. Both parts fit closely on into the other. The male part 114 comprises a face 133 and the female part 122 comprises a face 139. Both faces are intended to be applied one against the other to define said second fastening means. As illustrated, the male part makes an integral part of the fore part of the connection bar. It should be noticed that dotted lines appearing on the connection bar 113 illustrated in FIG. 8 are only present to delimit the position of the machine portion corresponding to the male part 114 and thus make easier the understanding of the invention.

The second and third of said association are identical and each comprises a male part 192 and a female part 196. Both parts fit closely one into the other. More particularly, they have lateral sides that cooperate together to prevent lateral motion of the suprastructure with respect to the connection bar 113. The male part 192 makes an integral part of a corresponding portion of the connection bar 113, said portion being positioned between the fore part and the rear part. Here again, the dotted line appearing in FIG. 8 are only present to delimits the male parts 192 and make easier the understanding of the invention.

Advantageously, the aforesaid first, second and third associations 102 and 192 are prefabricated and adjust to fit closely one into the other.

Figure 3:
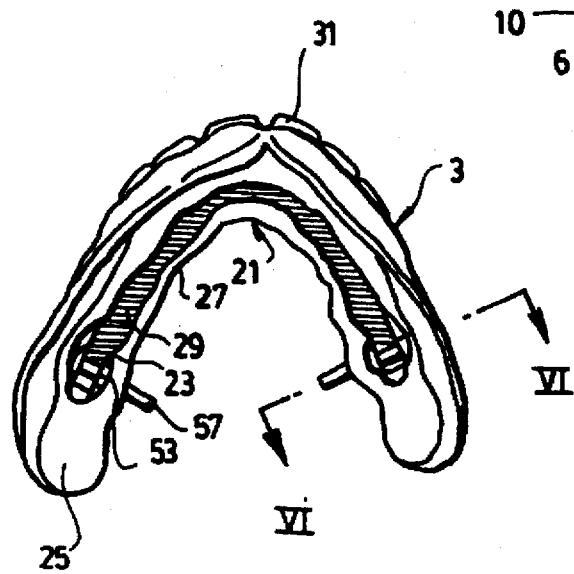
FIG. 3 is a top plan view of the suprastructure of a teeth prosthesis according to the invention with a pin in open position.
Figure 6:
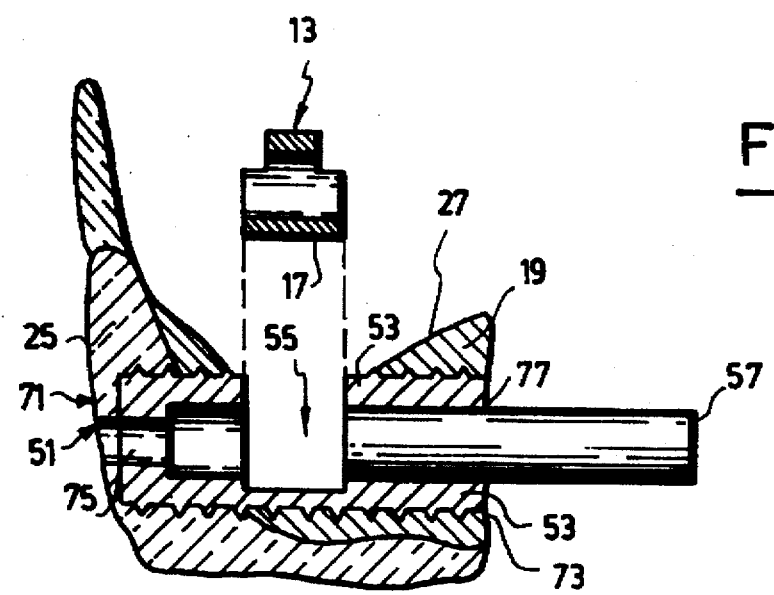
FIG. 6 is a cross-sectional view according to line VI—VI in FIG. 3 and line VI'—VI' of FIG. 1 with the pin in open position and the protuberance of the connection bar removed from the member.
Figure 7:
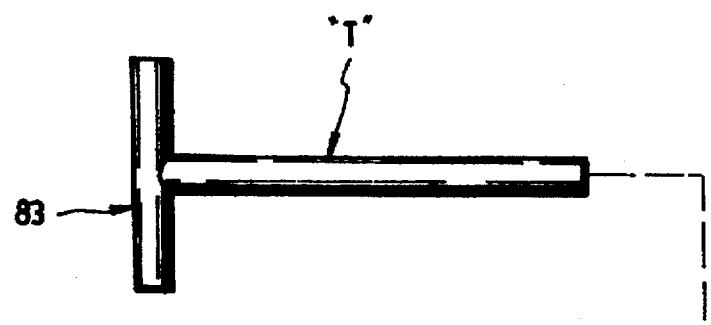
FIG. 7 is a cross-sectional view similar to the one of FIG. 6 except the protuberance of the connection bar of the infrastructure is aligned with the sleeve of the suprastructure.
Figure 7:
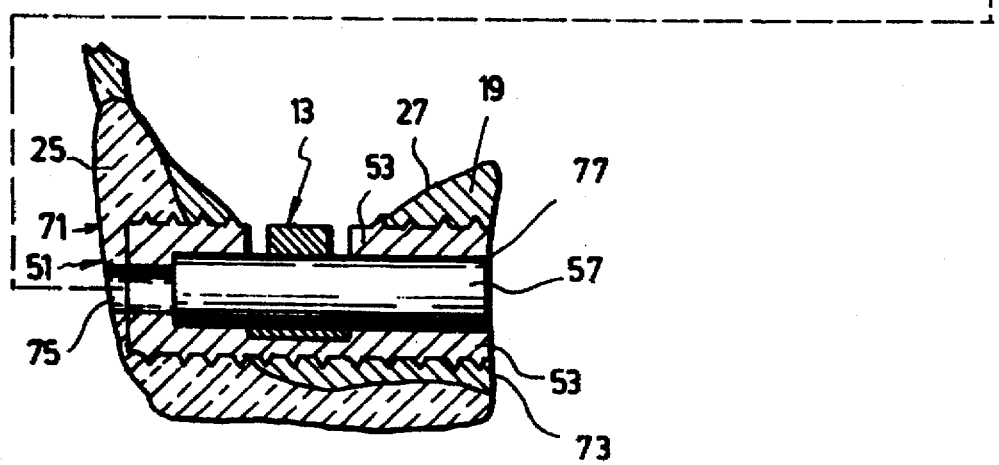
Figure 9:
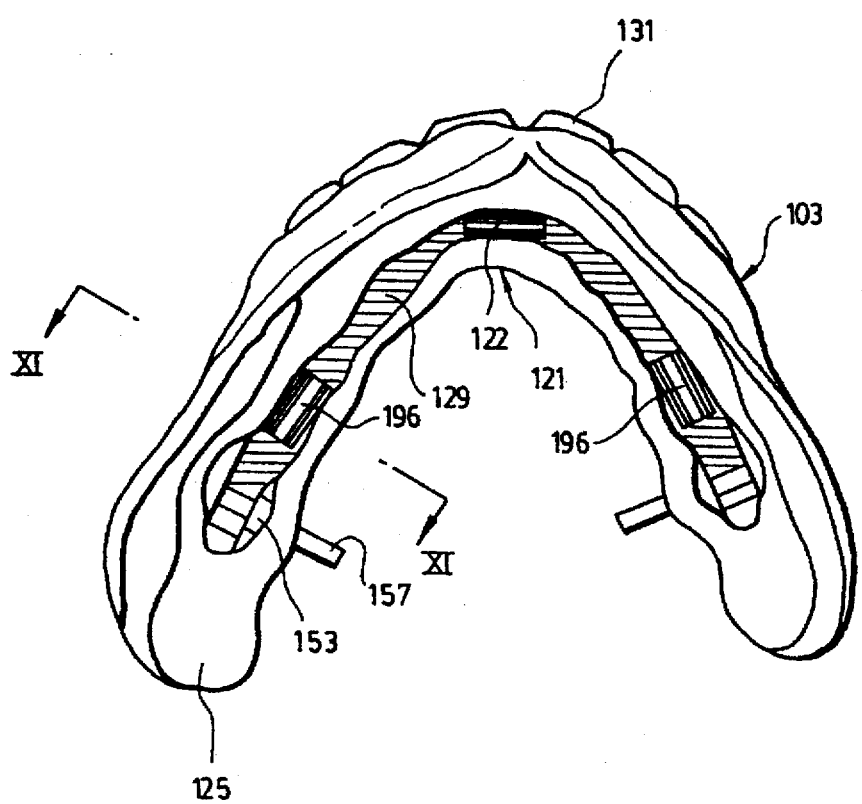
FIG. 9 is a front elevational view of a suprastructure manufactured with inserts according to a particularly preferred embodiment of the invention.
Figure 10:
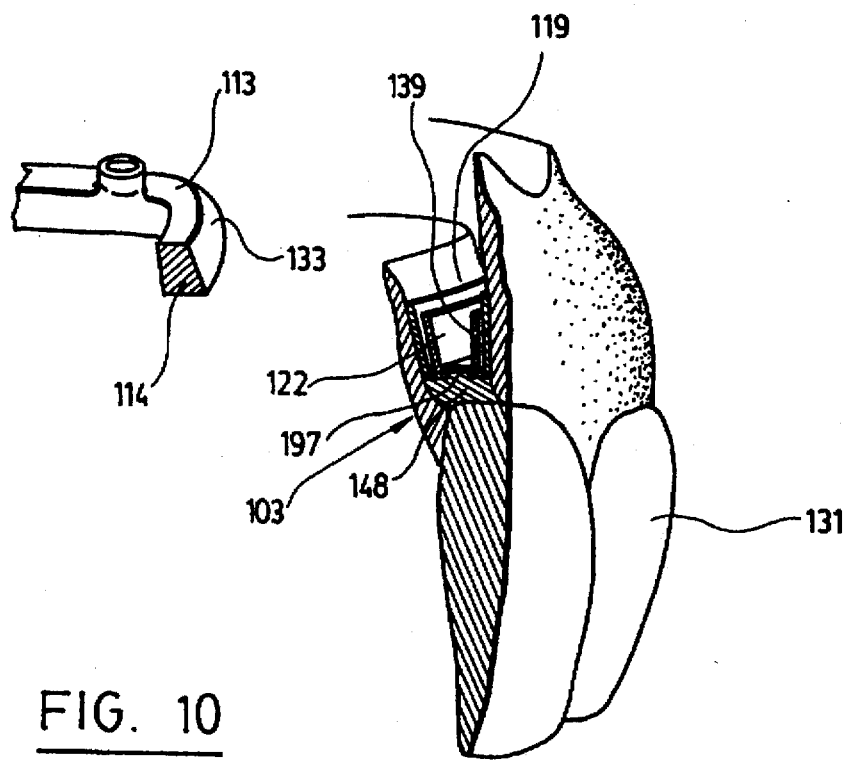
FIG. 10 is a cross sectional exploded side elevational view of the suprastructure and the connection bar of a teeth prosthesis according to a particularly preferred embodiment of the invention.
Figure 11:
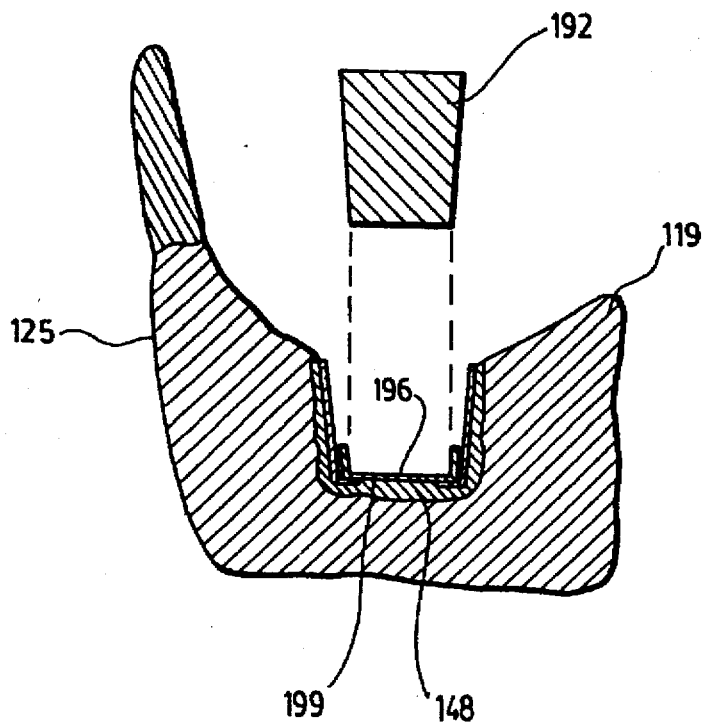
FIG. 11 is a cross sectional view of the suprastructure according to line XI—XI of FIG. 9 and a cross sectional view of the connection bar according to line XI'—XI' of FIG. 8.

In FIGS. 9 to 11 there is illustrated a particularly preferred suprastructure 103 similar to the one of FIG. 3 except female parts 122 and 196 have been fastened to the first member 119, more particularly in the housing 129. Each female part may be fastened to the first member by any appropriate means well known to man skilled in the art. Preferably, as illustrated in FIGS. 10 and 11, the female parts 122 and 196 are welded on the first member 119. When said female parts 122 and 196 are welded, it is advantageous to have a window 197 or 199 provided in the first member 119 to make easier the welding operation. Each female part 122 or 196 preferably contacts the first member only near the corresponding window (197 or 199), such windows 197 or 199 being of size slightly smaller that the corresponding female part 122 or 196.

More particularly, to use the preferred prosthesis "P'" defined hereinabove, the following steps may be carried out:

for mounting the suprastructure 103 on the infrastructure 101, one only have to grasp the fore part 121 of the suprastructure 103 and put sliding faces 133, 139 one against the other, to apply male parts 192 against corresponding female parts 196 (to have their lateral faces further preventing lateral motions of the first member with respect to the connection bar) and to house each protuberance 161 of the connection bar 113 in a corresponding housing of the member 119 to thus co-axially align the longitudinal axis of each bore 159 of the connection bar 113 with the longitudinal axis of a corresponding sleeve 113, and then to push each pin 157 with his finger or his tongue to slid them in their respective cylindrical sleeve 153 and through a corresponding bore 161 of the connection bar 113;

for removing the suprastructure 103 from the infrastructure 101 one only have to introduce a fine Pin (not shown but corresponding to the fine pin 83 shown in FIG. 7) through the said bore (not shown but corresponding to the bore 75 shown in FIG. 7) of the suprastructure 103 and push the pin 157 until it no longer face the lateral opening 153 of its corresponding cylindrical sleeve 153, to remove said fine pin 175 from said bore 175 and introduce it through the other bore of the suprastructure 103 and push the pin 157 until it no longer face the lateral opening 105 of its corresponding cylindrical sleeve 153, and then to grasp the fore part 121 of the suprastructure 103 and the male part 192 from the female part 196 and remove both sliding faces 133, 139 from each other.

Preferably, when sliding faces are slid one against the other during the mounting of the suprastructure 103 on the infrastructure 101 or the removing of the suprastructure 103 from the infrastructure 101, said faces are moved substantially parallel, (i.e. thus the suprastructure 103 is moved with respect to the infrastructure 101 according to an angle substantially parallel with a plane containing said sliding surface 133).

Figure 19:
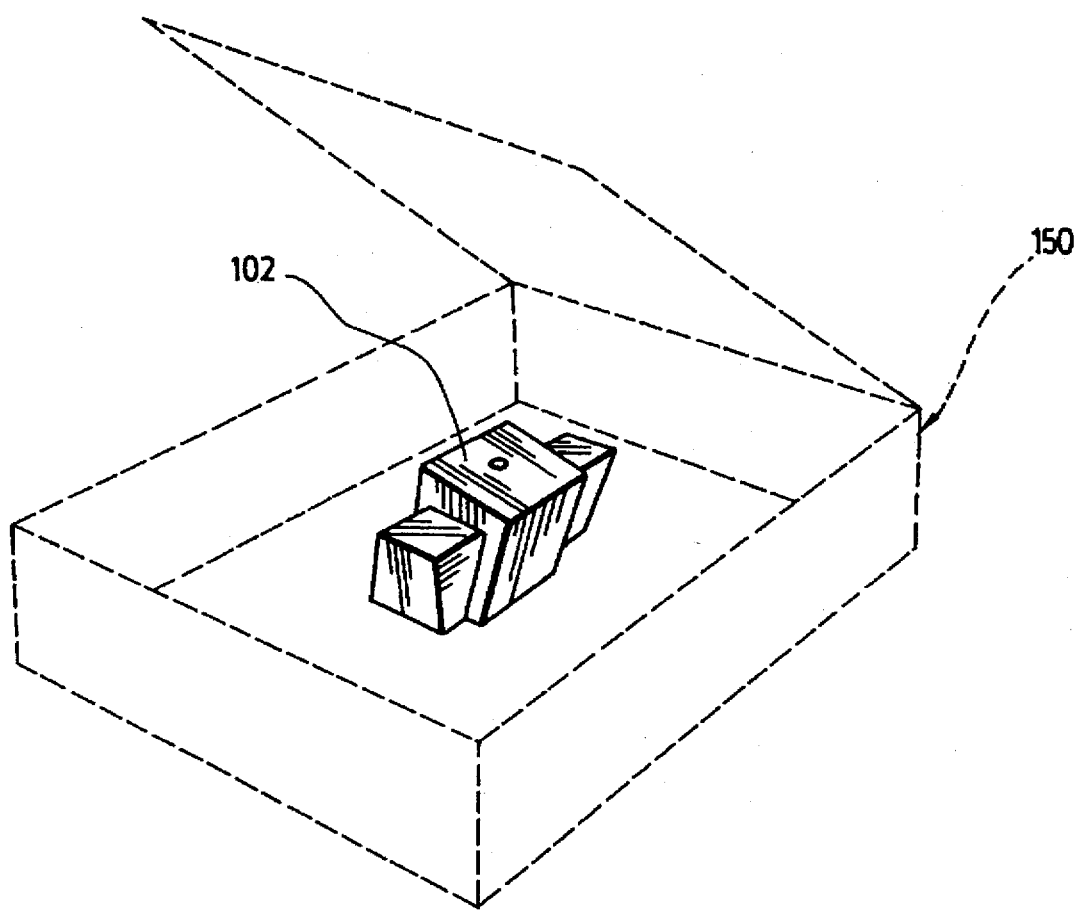
FIG. 19 is a front perspective view of a kit according to the invention.
Figure 20:
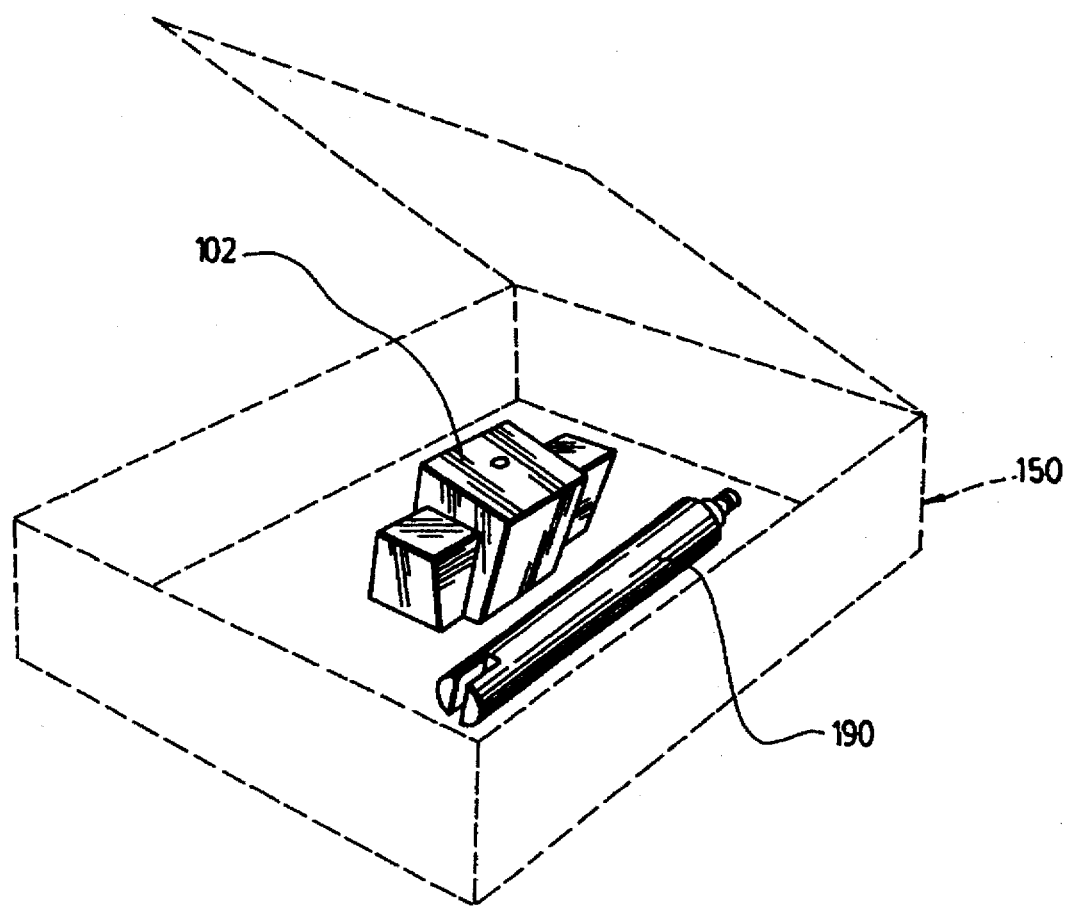
FIG. 20 is a front perspective view of an another kit according to the invention.
Figure 21:
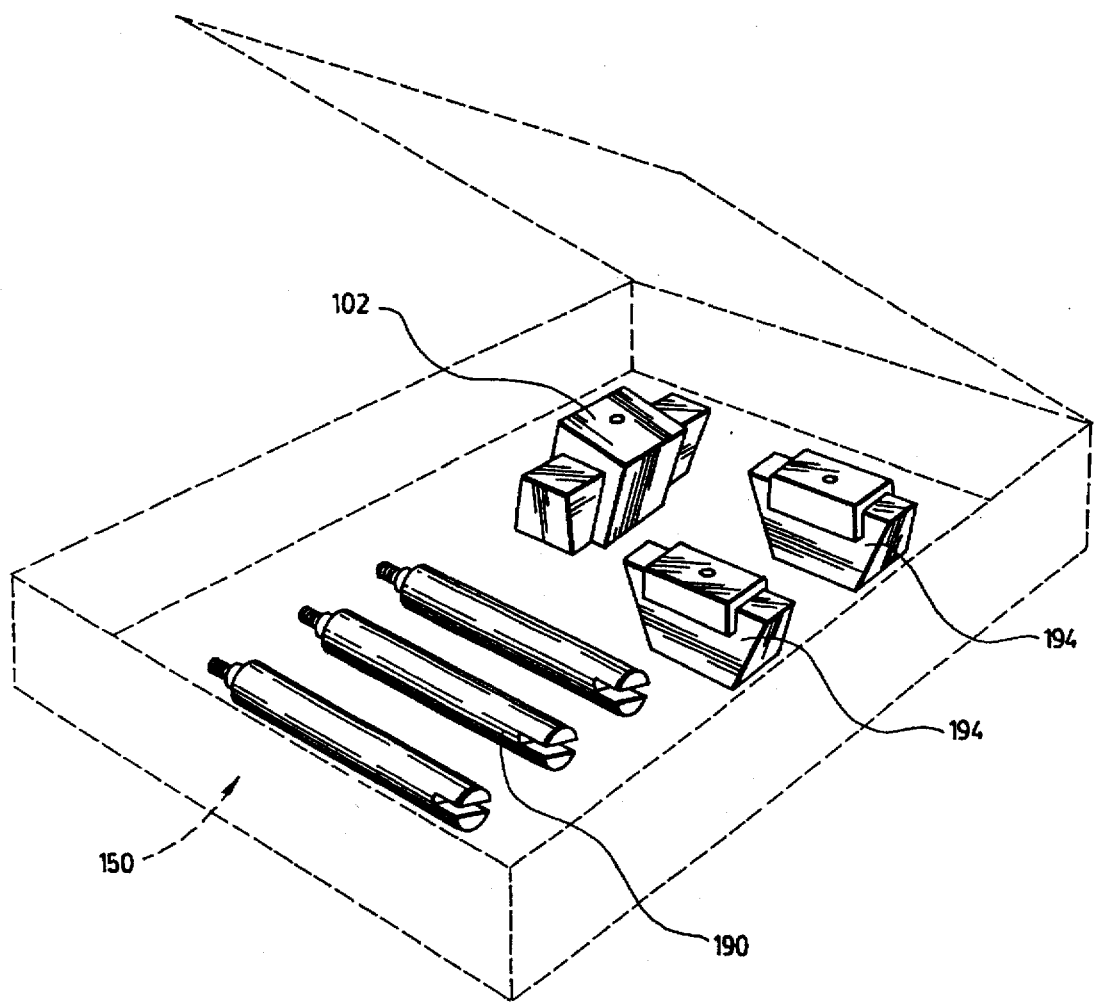
FIG. 21 is a front perspective view of an another kit according to the invention.

The invention also relates, with reference to FIGS. 19 to 21, to a kit comprising prefabricated parts useful for the manufacture of a teeth prosthesis "P'". More particularly, said kit comprises one two part insert 102. As better shown on FIGS. 12 to 14, the insert 102 comprises a female part 122 and a male part 114 which are manufactured to fit closely one into the other. The male part 114 and the female part 122 may he removably securable together with securing means. The two part insert 102 corresponds to the second fastening means. The male part 114 is to be incorporated in the connection bar while the female part 122 is to be fastened to the first member 119 (in the housing 129).

Figure 12:
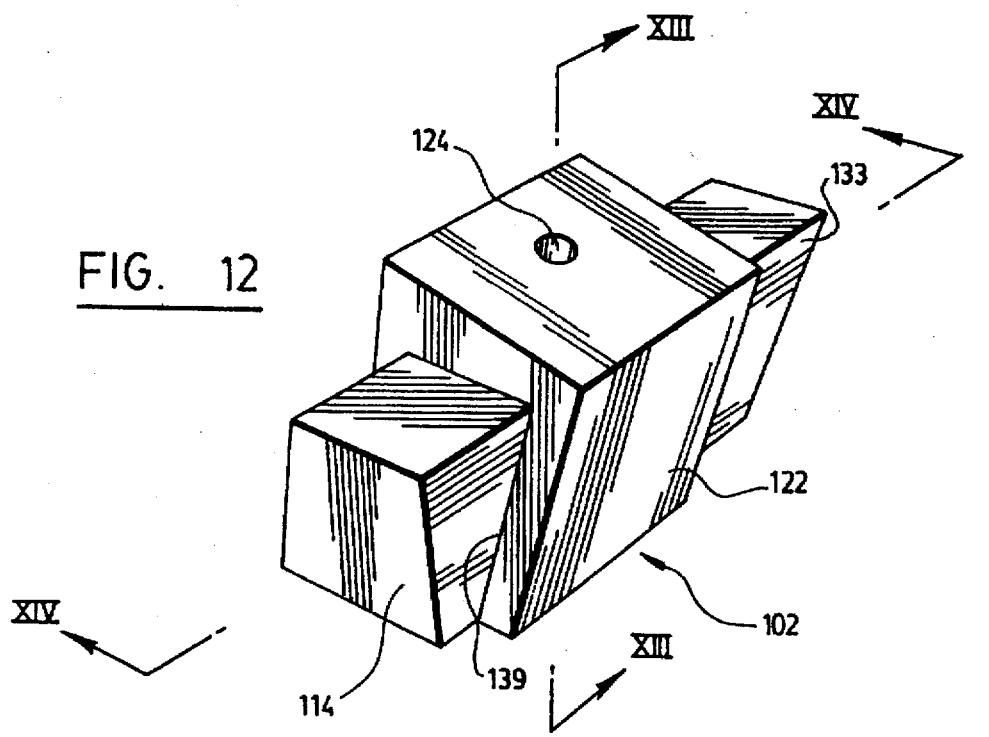
FIG. 12 is an elevational view of a first two part insert which is comprises in a kit according to the invention.
Figure 13:
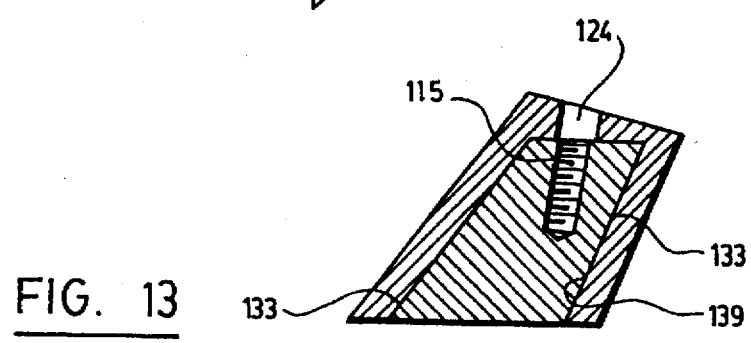
FIG. 13 is a cross-sectional view according to line XIII—XIII of FIG. 12.
Figure 14:
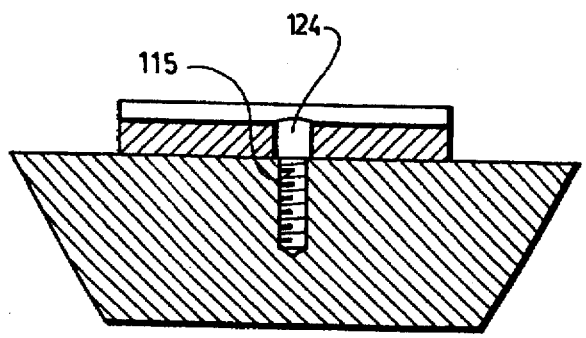
FIG. 14 is a cross-sectional view according to line XIV—XIV of FIG. 12.
Figure 15:
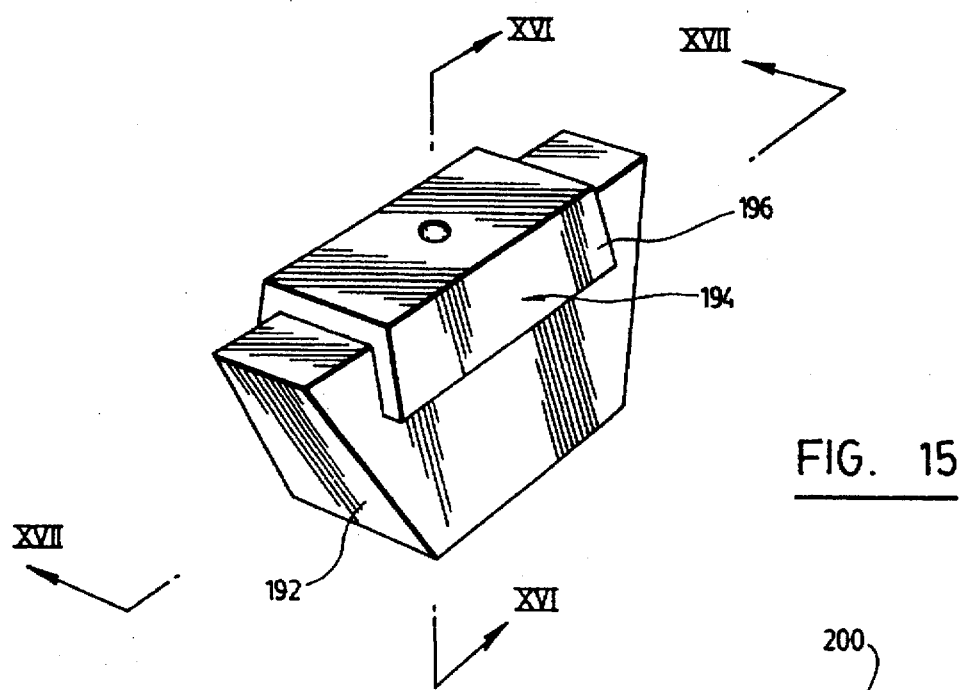
FIG. 15 is an elevational view of a two part insert which is comprises in a kit according to the invention.
Figure 16:
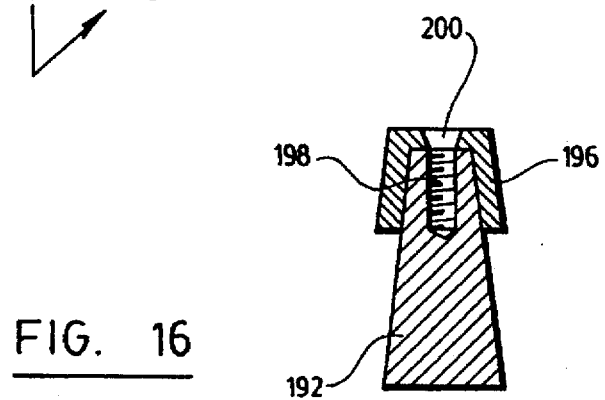
FIG. 16 is a cross-sectional view according to line XVI—XVI of FIG. 15.
Figure 17:
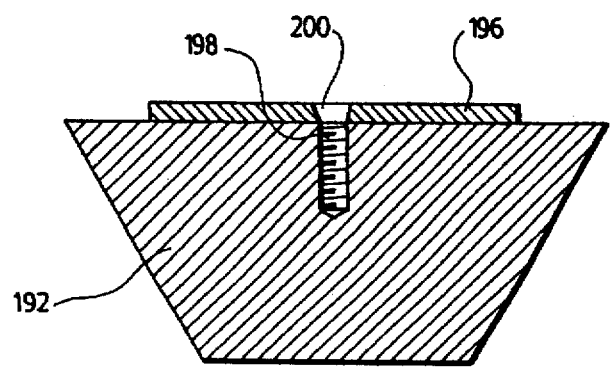
FIG. 17 is a cross-sectional view according to line XVII—XVII of FIG. 15.

According to a particularly preferred embodiment of the invention, the kit may comprise:

at least a first two part insert 102, also shown on FIGS. 12 to 14, comprising a female part 122 and a male part 114 which are manufactured to fit closely one into the other. The male part 114 and the female part 122 may be removably securable together with securing means. The two part insert 102 corresponds to said second fastening means. The male part 114 is to be incorporated with a connection bar 113 while the female part 122 is to be fastened to the first member 119;

at least a second and a third two part insert, 194. Referring now to FIGS. 15 to 17, each insert 194 comprises a female part 196 and a male part 192 which are manufactured to fit closely one into the other. The male part 192 and the female part 196 may be removably securable together with securing means. The male parts 192 are respectively to be incorporated with a connection bar 113 between the fore part and a corresponding opposite rear end Of the connection bar 113, while the female part 196 is to be fastened to the first member 119.

Referring and to FIG. 13 and 14, and according to a particularly preferred embodiment of the invention, securing means of the insert 102 may comprise a tapped hole 115 provided in the male part 114. A corresponding tapped hole 124 is provided in the female part 122 and coaxial with the hole 115 of the male part 114, and a threaded guide pin 190, said holes being to be engaged by said guide pin 190. Such securing means and more particularly such guide pin 190 may be advantageously comprised in the kit of the invention (as shown on FIG. 20).

Also, same kind of securing means as defined hereinabove may be provided on the second and third inserts 194. referring now to FIGS. 16 and 17 and according to a particularly preferred embodiment of the invention, securing means of the inserts 194 may comprise a tapped hole 198 provided in the male part 192, a corresponding tapped hole 200 provided in the female part 196 and coaxial with the hole 198 of the male part 192, and a threaded guide pin 190, said holes being to be engaged by said guide pin 190. As shown on FIG. 21 a kit according to the invention advantageously comprises three of such guide pins 190.

The kit may further comprise at least two first fastening means, especially fasteners of the type sold under the trade mark MK1 (Polydental Laboratory, BELGIUM).

Advantageously, the above kits may be optionally associated with an appropriate packaging and/or notice explaining how to use parts of the kit in order to embody a prosthesis "P". In FIGS. 19 to 21 an optional packaging 150 is represented with dotted lines.

The invention also relates to a method for the manufacture of the prosthesis "P", preferably starting with a kit as defined hereinabove.

More particularly, the invention relates to a method for the manufacture of a teeth prosthesis "P" as defined hereinabove and with particular references to FIGS. 8 to 11, wherein the connection bar 113 of the infrastructure 101 and the suprastructure 103 are obtained according to the following steps:

a) Building a pattern of a connection bar 113 with reference to a matrix which is a duplicate of the gingiva of an upper maxilla provided with at least three implants, then removing at least one portion of said pattern, said portion substantially corresponding to a male part 114 of a two parts insert 102, said two part insert comprising a female part 122 and the male part 114 and both parts being manufactured to fit closely one into the other. The male part 114 and the female part 122 are further removably securable together with securing means and corresponds to said second fastening means.

b) Obtaining one moulded member or several moulded member parts by casting of a metal or alloy in one or several moulds corresponding to the pattern or corresponding parts of the pattern. Then fastening it or them to the male part 114 to thus define said connection bar 113.

c) Building a first member mould from a matrix which is a duplicate of the gingiva of the upper maxilla provided with at least three implants, the connection bar 114 and the female part 122 of the two part insert 102 secured thereon.

d) obtaining the first member 119 by casting a metal or alloy thereof in the mould to fill this latter and then removing the resulting first member 119.

e) Removing the female part 122 from the male part 114 incorporated in the connection bar 113, and then fastening it with the first member 119 so as to be engageable by said male part 114 incorporated in the connection bar 113.

f) Positioning and securing the teeth 131, the saddle 125 and the first fastening means on the first member 119 to thus define the suprastructure 103.

Advantageously, the invention relates to a method for the manufacture of a teeth prosthesis "P" as defined hereinabove, wherein the connection bar 113 of the infrastructure 101 and the suprastructure 103 are obtained according to the following steps:

a) Building a pattern of a connection bar with reference to a matrix which is a duplicate of the gingiva of an upper maxilla provided with at least three implants, then removing at least three portions of said pattern, said portions substantially corresponding to male parts 114 and 192 of corresponding two part inserts 102 or 194. The two part insert 102 comprises a male part 114 and a female part 122. Each of said two part inserts 194 comprises a male part 192 and a female part 196. Both parts, 114 and 122, or, 192 and 196, are manufactured to fit closely one into the other. The male part 114 (or 192) and the female part 122 or (196) are further removably securable together with securing means. The male part 114 are to be located at the fore part of the connection bar 113. The male part 114 and the female part 122 corresponds to said second fastening means. The male part 192 are located on either side of the fore part the connection bar 113.

b) Obtaining one moulded member or several moulded member parts by casting of a metal or alloy in one or several moulds corresponding to the pattern or corresponding parts of the pattern, and then fastening it or them to the male parts 114 and 192 to thus define said connection bar 113.

c) Building a first member mould from a matrix which is a duplicate of the gingiva of the upper maxilla provided with at least three implants, the connection bar 113 and the female part 122 and 196 secured thereon, said mould being designed to define in the first member 119 to be obtained a cavity above each of the female parts. Preferably, said cavity is a window 197 or 199. This window 197 or 199 is preferably of smaller cross section than its corresponding female part.

d) Obtaining the first member 119 by casting a metal or alloy thereof in the mould to fill this latter and then removing the resulting first member 119.

e) Removing each female part 122 and 196 from a corresponding male part 114 and 192 incorporated in the connection bar 113, and then fastening them with the first member 119 so as to be engageable by said corresponding male part incorporated in the connection bar 113.

f) Positioning and securing the teeth 131, the saddle 125 and the first fastening means on the first member 119 to thus define the suprastructure 103.

Advantageously, securing means comprise a tapped hole 198 or 115 provided in the male part, a corresponding hole 200 or 124 in the female part and coaxial with the hole 198 or 115 of the male part, and a threaded guide pin 190, holes, 115 and 124, and 198 and 200, being to be engaged by a guide pin 190, respectively (see FIGS. 12 to 18).

Advantageously, the female part 122 and/or 196 are fastened to the first member 119 by any appropriate means, such as welding.

A matrix may be advantageously performed by successive moulding steps. Those steps are well known to persons skilled in dental technique. The connection bar mould may be obtained by using a wax model.

Advantageously the first member 119 may be obtained by using a wax model realized on the matrix (according to techniques well known in the are). This technique allows to cut windows in the model, said windows facing the together with a screw, or more preferably a threaded guide female part of each insert.

Figure 18:
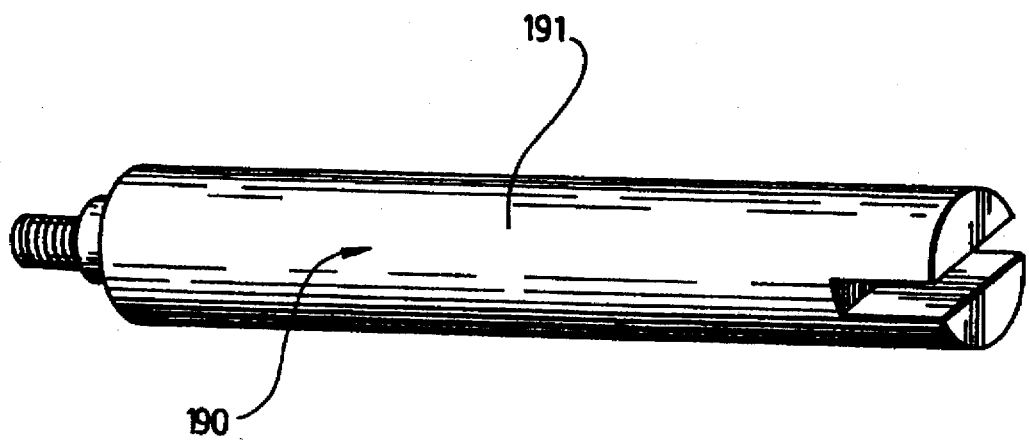
FIG. 18 is a front perspective view of a guide pin which is comprises in a kit according to the invention.

The male part and the female part may be removably secured together with a screw, or more preferably a threaded guide pin 190 like the one shown on FIG. 18, designed to engage the holes provided in both females and male parts. Such a guide pin 190 may advantageously presents a long and cylindrical head 191 projecting up above its threaded part to allow an easy installation and removal.

As well known in the art both the infrastructure and the suprastructure should be try on the person for whom the prosthesis is destined, to perform the usual and necessary adjustments of the different pieces of the prosthesis on the gingiva.

Preferably, as illustrated in FIGS. 10 and 11 of the drawings, the saddle 125 and the set of teeth 131 may be fastened to the first member 119 with a glue 148. Any type of glue commonly used in dentistry may be used.

Of course, the invention also relates to all variations that could be obvious to a man skilled in the art.

What is claimed is:

1. A teeth prosthesis for an upper maxilla, said prosthesis comprising an infrastructure, a suprastructure and means for a removable attachment of the suprastructure with the infrastructure;

said infrastructure comprising:
at least three implants, each implant having opposite ends, one end of each implant being anchored in a bone of an upper maxilla while an opposite end is sticking out of a gingiva and defines a head to said implant;
one connection bar having a fore part and two opposite rear ends, said bar being shaped and sized to be substantially facing the gingiva of the upper maxilla; and
means for removably fastening the connection bar with and against each head of said implants;

said suprastructure comprising:
a first member made of metal, and having a fore part and two rear ends, having an intrados provided with an opening giving access to a housing provided in the member, said housing being of such size and depth to allow the housing of the connection bar therein;
a second member immovably attached with the first member, said first and second members defining together a saddle; and
a set of teeth immovably attached with the first member and the second member;

said means for a removable attachment of the suprastructure and the infrastructure comprising:
two first fastening means that are respectively attached with a corresponding rear end of the members for removably attaching them with corresponding ends of the connection bar;
a second fastening means comprising a first sliding face provided on the fore part of the connection bar and inclined toward a rear of said connection bar, a lower part of said face forming with a bottom face of said connection bar an edge projecting ahead the connection bar, and a second sliding face provided on a fore wall of the housing of the first member, said sliding faces, when the first and second fastening means are attached with the connection bar, cooperating together to lock the fore part of the first member against the fore part of the connection bar and press a fore part of the saddle against a corresponding portion of gingiva of the upper maxilla;
wherein the connection bar has at least one first distinct machined portion that is sized and shaped to contact a corresponding first machined member secured inside the housing of the first member, an association machined portion—machined member being distributed in such a way in the prosthesis that said association is positioned at a fore part of said prosthesis and defined said second fastening means.

2. A teeth prosthesis according to claim 1, wherein said first fastening means respectively comprising:
a device that is attached with a corresponding end of the member, said device comprising a cylindrical sleeve provided with a lateral opening, and a pin slidably mounted inside the sleeve and movable between two distinct positions, a first distinct position being defined when the pin is not facing the lateral opening and a second distinct position being defined when the pin is facing the lateral opening,
a bore provided in a small protuberance near corresponding end of the connection bar, said protuberance being shaped and sized to be housed in a corresponding cylindrical sleeve through the lateral opening of said cylindrical sleeve and co-axial with a longitudinal axis of the cylindrical sleeve, said bore being removably engageable by said pin.

3. A teeth prosthesis according to claim 2, wherein the cylindrical sleeve and the pin are both of such size to be completely housed between an inner and an outer lateral walls of the suprastructure, when the pin is slid completely inside the cylindrical sleeve, and wherein a portion of the pin projects from the corresponding inner wall of the suprastructure when the pin is slid to be not facing the lateral opening of the cylindrical sleeve, a first bore co-axial with the longitudinal axis of the pin being provided in the corresponding inner wall of the suprastructure to allow the passage of the pin therethrough and a second bore of size smaller than a diameter of the pin and co-axial with the longitudinal axis of said pin being provided in the corresponding outer wall of the suprastructure, said second bore allowing a small tool to push the pin from a distinct position where it faces the lateral opening of the cylindrical sleeve toward the other distinct position where said pin does not face said lateral opening.

4. A teeth prosthesis according to claim 3, wherein at least four implants are provided.

5. A teeth prosthesis according to claim 4, wherein five or six implants are provided.

6. A teeth prosthesis according to claim 3, wherein four implants are provided and wherein each implant is made with titanium metal or alloys.

7. A teeth prosthesis according to claim 3, wherein the suprastructure is further provided with a lip support.

8. A method of use of a teeth prosthesis as defined in claim 3, wherein:
for mounting the suprastructure on the infrastructure, the sliding surface of the infrastructure is slid against the sliding surface of the infrastructure, each protuberance of the connection bar is housed in a lateral opening of a corresponding sleeve of the first member to thus co-axially align the longitudinal axis of each bore of the connection bar with the longitudinal axis of a corresponding sleeve, and then each pin is moved along its or his tongue to cylindrical sleeve and through a corresponding bore of the connection bar;
for removing the suprastructure from the infrastructure, a fine pin is engaged through a first of said second bores of the suprastructure and push the pin until it no longer face the lateral opening of its corresponding cylindrical sleeve, removed from said first of said second bore, introduced through a second of said second bore of the suprastructure to push the pin until it no longer faces the lateral opening of its corresponding cylindrical sleeve, and then both sliding faces are moved away from each other and the protuberances are removed from the lateral opening of corresponding cylindrical sleeve of the first member.

9. A method according to claim 8, wherein when sliding faces are slid one against the other during the mounting of the suprastructure on the infrastructure or the removing of the suprastructure from the infrastructure, said faces are moved substantially parallel.

10. A method for the manufacture of a teeth prosthesis as defined in claim 2, wherein the connection bar of the infrastructure and the suprastructure are obtained according to the following steps:

building a pattern of the connection bar with reference to a matrix which is a duplicate of the gingiva of the upper maxilla provided with at least three implants, then removing at least three portions of said pattern, each said portion substantially corresponding to a male part of a corresponding two part insert, each of said two part inserts comprising a female part and a male part and both parts being manufactured to fit closely one into the other, the male part and the female part being further removably securable together with securing means, the male part of a first of said two part inserts being to be located at the fore part of the connection bar, said first two part insert corresponding to said second fastening means, and the male part of a second and of a third of said two part inserts being located on either side of the fore part the connection bar;

obtaining at least one moulded member part by casting of a metal in at least one mould corresponding to the pattern, and then fastening the moulded member part to the male parts to thus define said connection bar;

building a first member mould from a matrix which is a duplicate of the gingiva of the upper maxilla provided with at least three implants, the connection bar and the female part of the two part inserts secured thereon, said first member mould being designed to define in the first member to be obtained a cavity above each of the female parts;

obtaining the first member by casting a metal thereof in the first member mould to fill the first member and then removing the resulting first member;

removing each female part from a corresponding male part incorporated in the connection bar, and then fastening the female part with the first member so as to be engageable by said corresponding male part incorporated in the connection bar; and positioning and securing the teeth, the saddle and the first fastening means on the first member to define the suprastructure.

11. A method according to claim 10, wherein each cavity is a window, and wherein each cavity is smaller than a corresponding female part.

12. A method according to claim 11, wherein the female part is fastened to the first member by welding.

13. A method according to claim 10, wherein said securing means comprise a tapped hole provided in the male part, a corresponding hole in the female part and coaxial with the hole of the male part, and a threaded guide pin, said holes being to be engaged by said guide pin.

14. A method according to claim 10, wherein the female part is fastened to the first member by welding.

15. A teeth prosthesis according to claim 1, wherein the connection bar has at least three of said at least one distinct machined portions, that are each sized and shaped to contact a corresponding machined member secured inside the housing of the first member, each association machined portion—machined member being distributed in such a way in the prosthesis that a first association is positioned at a fore part of said prosthesis, said first association defining said second fastening means, while second and third associations are respectively positioned between the first association and a corresponding first fastener.

16. A method of use of a teeth prosthesis as defined in claim 1, wherein:

for mounting the suprastructure on the infrastructure, both sliding surfaces are moved one against the other and the rear ends of the member are fastened with the corresponding rear ends of the connection bar;

for removing the suprastructure from the infrastructure, the rear ends of the member are unfastened from the corresponding rear ends of the connection bar and the sliding faces are moved away from each other.

17. A method for them anufaotUre of a teeth prosthesis as defined in claim 1, wherein the connection bar of the infrastructure and the suprastructure are obtained according to the following steps:

a) building a pattern of a connection bar with reference to a matrix which is a duplicate of the gingiva of an upper maxilla provided with at least three implants, then removing at least one portion of said pattern, said portion substantially corresponding to a male part of a two parts insert, said two part insert comprising a female part and the male part and both parts being manufactured to fit closely one into the other, the male part and the female part being further removably securable together with securing means and corresponding to said second fastening means;

b) obtaining one moulded member or several moulded member parts by casting of a metal or alloy in one or several mould corresponding to the pattern or corresponding parts of the pattern, and then fastening it or them to the male part to thus define said connection bar;

c) building a first member mould from a matrix which is a duplicate of the gingiva of the upper maxilla provided with at least three implants, the connection bar and the female part of the two part insert secured thereon;

d) obtaining the first member by casting a metal or alloy thereof in the mould to fill this latter and then removing the resulting first member;

e) removing the female part from the male part incorporated in the connection bar, and then fastening it with the first member so as to be engageable by said male part incorporated in the connection bar; and f) positioning and securing the teeth, the saddle and the first fastening means on the first member to thus define the suprastructure.

18. A method according to claim 17, wherein said securing means comprise a tapped hole provided in the male part, a corresponding hole in the female part and coaxial with the hole of the male part, and a threaded guide pin, said holes being to be engaged by said guide pin.

19. A kit comprising prefabricated parts useful for manufacture of a teeth prosthesis, said prosthesis comprising an infrastructure, a suprastructure, and means for a removable attachment of the suprastructure with the infrastructure;

said infrastructure comprising:
  at least three implants, each implant having opposite ends, one end of each implant being anchored in a bone of an upper maxilla while an opposite end is sticking out of the gingiva and defines a head to said implant;
  one connection bar having a fore part and two opposite rear ends, said connection bar being shaped and sized to be substantially facing the gingiva of the upper maxilla;
  means for removably fastening the connection bar with and against each head of said implants;
said suprastructure comprising:
  a first member made of metal, and having a fore part and two rear ends, having an intrados provided with an opening giving access to a housing provided in the first member, said housing being of such size and depth to allow the housing of the connection bar therein;
  a second member immovably attached with the first member, said first and second members defining together a saddle; and
  a set of teeth immovably attached with the first member and the second member;
said means for a removable attachment of the suprastructure and the infrastructure comprising:
  two first fastening means that are respectively attached with a corresponding rear end of the first and second members for removably attaching the members with corresponding ends of the connection bar;
  a second fastening means comprising a first sliding face provided on the fore part of the connection bar and inclined toward a rear of said connection bar, a lower part of said face forming with a bottom face of said connection bar an edge projecting ahead the connection bar, and a second sliding face provided on a fore wall of the housing of the first member, said sliding faces, when the first and second fastening means are attached with the connection bar, cooperating together to lock a fore part of the first member against the fore part of the connection bar and press a fore part of the saddle against the corresponding portion of the gingiva of the upper maxilla;
wherein the connection bar has at least a first distinct machined portion that is sized and shaped to contact a corresponding first machined member secured inside the housing of the first member, an association machined portion—machined member being distributed in such a way in the prosthesis that said association is positioned at a fore part of said prosthesis and defined said second fastening means;
said kit further comprising at least one two part insert, said two part insert comprising a female part and a male part which are manufactured to fit closely one into the other, the male part and the female part being removably securable together with securing means, and said two part insert corresponding to said second fastening means, the male part being to be incorporated in the connection bar while the female part is to be incorporated in the first member.

20. A kit according to claim 19, wherein said securing means comprise a tapped hole provided in the male part, a corresponding tapped hole provided in the female part and coaxial with the hole of the male part, and a threaded guide pin, said holes being to be engaged by said guide pin.

21. A kit according to claim 19, wherein it further comprise at least two first fastening means.

22. A kit according to claim 1, wherein it further comprises an explanatory notice.

23. A kit according to claim 19, wherein it is further associated with a packaging.

24. A kit for manufacture of a teeth prosthesis, said prosthesis comprising an infrastructure, a suprastructure, and means for a removable attachment of the suprastructure with the infrastructure;

said infrastructure comprising:
  at least three implants, each implant having opposite ends, one end of each implant being anchored in a bone of an upper maxilla while an opposite end is sticking out of the gingiva and defines a head to said implant;
  one connection bar having a fore part and two opposite rear ends, said connection bar being shaped and sized to be substantially facing the gingiva of the upper maxilla;
  means for removably fastening the connection bar with and against each head of said implants;
said suprastructure comprising:
  a first member made of metal, and having a fore part and two rear ends, having an intrados provided with an opening giving access to a housing provided in the first member, said housing being of such size and depth to allow the housing of the connection bar therein;
  a second member immovably attached with the first member, said first and second members defining together a saddle; and
  a set of teeth immovably attached with the first member and the second member;
said means for a removable attachment of the suprastructure and the infrastructure comprising:
  two first fastening means that are respectively attached with a corresponding rear end of the first and second members for removably attaching the members with corresponding ends of the connection bar;
  a second fastening means comprising a first sliding face provided on the fore part of the connection bar and inclined toward a rear of said connection bar, a lower part of said face forming with a bottom face of said connection bar an edge projecting ahead the connection bar, and a second sliding face provided on a fore wall of the housing of the first member, said sliding faces, when the first and second fastening means are attached with the connection bar, cooperating together to lock a fore part of the first member against the fore part of the connection bar and press a fore part of the saddle against the corresponding portion of the gingiva of the upper maxilla;
wherein the connection bar has at least three distinct machined portions that are each sized and shaped to contact a corresponding machined member secured inside the housing of the first member, each association machined portion—machined member being distributed in such a way in the prosthesis that a first association is positioned at a fore part of said prosthesis, said first association defining said second fastening means, while second and third associations are respectively positioned between the first association and a corresponding first fastener;
said kit further comprising:
  at least a first two part insert comprising a female part and a male part which are manufactured to fit closely one into the other, the male part and the female part being removably securable together with securing means, and said first two-part insert corresponding to said second fastening means, the male part of said two part insert being to be incorporated with the connection bar while the female part is to be incorporated in the first member;

at least a second of two part insert and a third two part insert, each comprising a female part and a male part which are manufactured to fit closely one into the other, the male part and the female part being removably securable together with securing means, and the male part of said second and third two part inserts being respectively to be incorporated with the connection bar between the fore part and the corresponding opposite rear end of said connection bar.

25. A kit according to claim 24, wherein said securing means comprise a tapped hole provided in the male part, a corresponding tapped hole provided in the female part and coaxial with the hole of the male part, and a threaded pin, said holes being to be engaged by said pin.

26. A kit according to claim 24, wherein it further comprise at least two first fastening means.

27. A kit comprising parts for the manufacture of a teeth prosthesis, said prosthesis comprising an infrastructure, a suprastructure, and means for a removable attachment of the suprastructure with the infrastructure;

said infrastructure comprising;
at least three implants, each implant having opposite ends, one end of each implant being anchored in a bone of an upper maxilla while an opposite end is sticking out of the gingiva and defines a head to said implant;
one connection bar having a fore part and two opposite rear ends, said connection bar being shaped and sized to be substantially facing the gingiva of the upper maxilla;
means for removably fastening the connection bar with and against each head of said implants;

said suprastructure comprising:
a first member made of metal, and having a fore part and two rear ends, having an intrados provided with an opening giving access to a housing provided in the first member, said housing being of such size and depth to allow the housing of the connection bar therein;
a second member immovably attached with the first member, said first and second members defining together a saddle; and
a set of teeth immovably attached with the first member and the second member;

said means for a removable attachment of the suprastructure and the infrastructure comprising:
two first fastening means that are respectively attached with a corresponding rear end of the first and second members for removably attaching the members with corresponding ends of the connection bar;

a second fastening means comprising a first sliding face provided on the fore part of the connection bar and inclined toward a rear of said connection bar, a lower part of said face forming with a bottom face of said connection bar an edge projecting ahead the connection bar, and a second sliding face provided on a fore wall of the housing of the first member, said sliding faces when the first and second fastening means are attached with the connection bar, cooperating together to lock a fore part of the first member against the fore part of the connection bar and press a fore part of the saddle against the corresponding portion of the gingiva of the upper maxilla;

wherein the connection bar has at least three distinct machined portions that are each sized and shaped to contact a corresponding machined member secured inside the housing of the first member, each association machined portion—machined member being distributed in such a way in the prosthesis that a first association is positioned at a fore part of said prosthesis, said first association defining said second fastening means, while second and third associations are respectively positioned between the first association and a corresponding first fastener;

said kit further comprising:
three threaded guide pins;
at least a first two part insert comprising a female part and a male part which are manufactured to fit closely one into the other, the male part and the female part being removably securable together with securing means, said securing means comprising a tapped hole provided in the male part, a corresponding hole provided in the female part and coaxial with the hole of the male part, said holes being engageable by a guide pin, and the male part of said two part insert being to be incorporated with a connection bar so as to define with said female part said second fastening means;
at least a second two part insert and a third two part insert, each comprising a female part and a male part which are manufactured to fit closely one into the other, the male part and the female part being removably securable together with securing means, said securing means comprising a tapped hole provided in the male part, a corresponding hole provided in the female part and coaxial with the hole of the male part, said holes being engageable by a corresponding guide pin, and the male part of said two part inserts being respectively to be incorporated with a connection bar between the fore part and a corresponding opposite rear end of said connection bar; and
at least two first fastening means.

28. A kit according to claim 27, wherein it further comprises an explanatory notice.

29. A kit according to claim 27, wherein it is further associated with a packaging.

* * * * *